United States Patent [19]

Collins et al.

[11] 4,113,758

[45] Sep. 12, 1978

[54] PROCESS FOR PREPARING ORGANOTIN HALIDES

[75] Inventors: John D. Collins, Albrighton; Trevor E. Jones, Halesowen, both of England

[73] Assignee: Albright & Wilson Ltd., Warley, England

[21] Appl. No.: 781,118

[22] Filed: Mar. 25, 1977

[30] Foreign Application Priority Data

Mar. 30, 1976 [GB] United Kingdom ............... 12693/76

[51] Int. Cl.$^2$ .............................................. C07F 7/22
[52] U.S. Cl. .................................................. 260/429.7
[58] Field of Search ....................................... 260/429.7

[56] References Cited

U.S. PATENT DOCUMENTS

| | | | |
|---|---|---|---|
| 3,402,189 | 9/1968 | Natoli | 260/429.7 |
| 3,609,173 | 9/1971 | Kushlefsky | 260/429.7 |

*Primary Examiner*—Helen M. S. Sneed
*Attorney, Agent, or Firm*—Flynn & Frishauf

[57] ABSTRACT

Tricycloalkyltin halides, e.g. tricyclohexyltin chloride, which is an intermediate for making the biocide tricyclohexyl tin hydroxide, are made by adding a solution of the cyclo alkyl magnesium halide in an ether to a solution of stannic halide in a liquid diluent, the weight percentage of stannic halide to diluent being less than 25%.

17 Claims, No Drawings

PROCESS FOR PREPARING ORGANOTIN HALIDES

This invention relates to a process for preparing organotin halides, in particular tricyclohexyltin halides.

Tricyclohexyltin chloride may be prepared by reaction of a cyclohexyl Grignard reagent and stannic chloride in a 3:1 molar ratio. The addition of the stannic chloride to the Grignard reagent produces a low yield of tricyclohexyl tin chloride with much tetracyclohexyltin. The reverse addition of the Grignard reagent to the stannic chloride is also known from BP No. 1084076 to give tricyclo hexyltin chloride, and in particular when the Grignard reagent and some of the stannic chloride are added simultaneously to the rest of the stannic chloride, with subsequent addition of the rest of the Grignard reagent, an 87% yield of tricyclo hexyltin chloride is stated to be formed.

We have now found a reverse addition process which is simpler than the latter process and can give a good yield of the desired tricyclohexyltin halides (and their nuclear alkylated products) and corresponding hydroxides obtained therefrom.

In one aspect the present invention provides a process for preparing triorganotin halides, which comprises adding 3 ± 0.3 molar proportions of a cyclo alkyl magnesium halide Grignard reagent, in which the cycloalkyl group is a cyclo hexyl group or an alkyl cyclohexyl group in which there are 1-3 alkyl groups each of 1-4 carbon atoms and in which the halide is a chloride, bromide or iodide, to one molar proportion of a stannic halide, in which the halide is chloride, bromide, or iodide, the cycloalkyl magnesium halide being dissolved in an ether solvent and the stannic halide being in an inert liquid diluent, the weight percentage of stannic halide to diluent being less than 25% and the addition being carried out with agitation to give a reaction mixture comprising a tricycloalkyl tin halide. Preferably, after the addition is complete, the reaction mixture is maintained for at least 5 minutes to progress the reaction further, e.g. at a temperature of at least 40° C., e.g. 40°–150° C., especially 90°–150° C.

The concentration of Grignard reagent in the ether can vary over a wide range but the stannic halide is present in less than 25% weight concentration in the diluent (i.e. weight percentage of stannic halide to diluent), e.g. 5–25% such as 9–15% or 10–25% e.g. 10–20% especially 15–20% or 15–25%. The Grignard reagent is usually in 15–80% weight concentration in the ether (i.e. the weight percentage of Grignard reagent to ether), e.g. 40–80% such as 40–70%, preferably 50–65%, and especially 53–60% concentration.

The cycloalkyl group in the cycloalkyl magnesium halide Grignard reagent may be a cyclohexyl group or an alkyl cyclohexyl group with 1 or 2 alkyl groups in the ring each of 1 or 2 carbon atoms. While the cycloalkyl group is preferably a cyclohexyl group, other examples are methyl and ethyl cyclohexyl groups. Preferably the halide in the cycloalkyl magnesium halide and the stannic halide are the same and preferably the chloride.

The Grignard reagent is made from the corresponding cycloalkyl halide with magnesium in a conventional manner. The reaction may be initiated if needed by addition of iodine, an iodide and in the case of cycloalkyl chlorides with a little of the corresponding cycloalkyl bromide. The reaction is usually carried out in an ether solvent, such as diethyl ether or tetrahydrofuran; advantageously the ether solvent is the same one as is to be used in the process of the invention. Thus preferably the Grignard reagent is prepared in the ethereal solution, the solution filtered to remove any unreacted magnesium or other insolubles and then is ready for use in the process of the invention. The preparation of the Grignard reagent, its subsequent handling and reaction with the stannic halide are all preferably carried out with exclusion of moisture, e.g. by maintenance of an inert atmosphere of, e.g. nitrogen gas.

The ether solvent for the Grignard reagent is preferably of formula $R_1 — (OR_3)_n — OR_2$, wherein (i) each of $R_1$ and $R_2$, which may be different but are preferably the same, is an alkyl group of 1 to 6 carbon atoms, and $R_3$ is an alkylene group of 1 to 4 carbon atoms, usually 2 or 3 carbon atoms and $n$ is 0 or 1, or (ii), when $n$ is 0, $R_1$ and $R_2$ together form a divalent radical of 4 or 5 chain members, which is a divalent saturated or ethylenically unsaturated aliphatic (usually an aliphatic hydrocarbyl) group, in which the carbon atom chain may optionally be interrupted by an oxygen atom or

group, where $R_4$ is an alkyl group of 1 to 4 carbon atoms. Thus the ether may be, when $n$ is 0, a simple di alkyl ether containing 1 to 6 carbon atoms, or, when $n$ is 1, a glycol diether in which $R_3$ is an ethylene radical, or, when $n$ is 0, a cyclic ether of 5 or 6 ring atoms in which $R_1$ and $R_2$ together form a divalent group. Examples of the dialkyl ether are diethyl, dipropyl, diisopropyl, di-n-butyl, di n- and isoamyl and di-n- hexyl ether. Examples of the glycol diether are ethylene glycol dimethyl, diethyl and di-n-butyl ethers. Examples of cyclic ethers are tetrahydrofuran, 2-methyl tetrahydrofuran, 2-methoxy- and 2-ethoxy-methyl tetrahydrofuran, tetrahydropyran, 2-methoxy 2-ethoxy tetrahydropyran, N-methyl morpholine and dioxan. Preferably, the ether has a total of 4–8 carbon atoms and 1 or 2 oxygen atoms; examples of such ethers are diethyl, diisopropyl, dipropyl and dibutyl ethers, the dimethyl and diethyl ethers of ethylene glycol, dioxan and tetrahydrofuran, which is most preferred. The ether preferably has a boiling point under the reaction pressure usually atmospheric pressure of less than 105° C. and especially less than 90° C., e.g. 35°–90° C.

The inert liquid diluent, in which is the stannic halide, is usually a solvent for the stannic halide and is usually a hydrocarbon. Examples of the diluent are aliphatic hydrocarbons, e.g. "petroleum ethers" of boiling points in the 60°–140° C. region, especially 100°–120° C. and 120°–140° C., cycloaliphatic hydrocarbons, e.g. cyclohexane, aromatic hydrocarbons, e.g. benzene and alkyl benzenes such as toluene and xylene. Preferably the inert diluent has a boiling point under the reaction pressure of at least 105° C. Examples of such preferred diluents are toluene and xylene. Xylene is most preferred.

The Grignard reagent in the ether solution is added to an agitated mixture of diluent and the stannic halide; in contrast to the known process, the Grignard reagent is added to all the halide and no stannic halide is added simultaneously with the Grignard reagent, and also there is no subsequent separate addition of extra diluent after the reaction has started. In the addition the Grignard reagent is added to the stannic chloride to form a reaction mixture comprising stannic chloride and an initial reaction product and then further Grignard reagent is added to this reaction mixture until all the Grignard reagent has been added, the total molar proportion of the Grignard reagent added to stannic chloride being 2.7:1 to 3.3:1 e.g. 2.7:1 to 2.95:1 but preferably 2.8:1 to 3.05:1, e.g. 2.9:1 to 3.05:1, especially about the stoichiometric value of 3:1.

As the reaction proceeds, the reaction mixture becomes more viscous. In the previous inverse addition process, the weight percentage of the diluent, xylene, to the total weight of xylene and ether, which was tetrahydrofuran, in the reaction mixture, was about 22–40%, i.e. the reaction mixture was predominantly tetrahydrofuran. We have now found that the reaction proceeds very advantageously when the weight percentage of diluent, e.g. xylene to the total weight of diluent and ether, e.g. tetrahydrofuran in the reaction mixture is 50–80%, e.g. 60–76%, though percentages some of which fall outside the range, e.g. 30–80% may be used.

The addition of cycloalkyl magnesium halide Grignard reagent to the stannic halide is usually carried out at a temperature up to 105° C. such as 20°–105° C., e.g. 40°–95° C. and especially 70°–85° C.

The solution of Grignard reagent is usually added to the stannic halide and diluent slowly at a rate sufficient to maintain the reaction mixture at the above temperature. The reaction may, if necessary, be carried out under pressure if the reaction temperature is above the boiling point at atmospheric pressure of the mixture of ether and liquid diluent in order to maintain the mixture liquid. Conveniently, in the preferred process, in which the ether has a boiling point of less than 90° C., the Grignard reagent is added at a rate sufficient to cause the reaction mixture to boil with the ether refluxing. With the preferred ether, tetrahydrofuran, the reaction liquid temperature is in the 75°–85° C. region.

In a preferred process the ether has a boiling point less than that of the diluent and at least some, e.g. some and preferably a major proportion of the ether in said reaction mixture after addition of Grignard reagent is evaporated leaving a medium comprising tricycloalkyltin halide but depleted of the ether. Usually 20–90% of the ether is evaporated and especially 50–80%. While the evaporation can occur under reduced pressure the evaporation is usually carried out by heating the mixture of ether, diluent and reaction product under atmospheric pressure to a second reaction temperature which is above the boiling point of the ether so that the ether distils off and the distillate can be collected for reuse. The second temperature is usually in the range 60°–150° C., e.g. 90°–150° C., preferably 105°–150° C. and especially 110°–150° C. Usually, once the ether has been distilled off, the reaction mixture is maintained at the second reaction temperature for a period of time, e.g. at least 0.5 hour preferably for 1–4 hr. Conveniently, the further heating is carried out by refluxing the liquid in the reaction mixture, the liquid containing usually a major proportion of diluent and a minor proportion of the ether. The total time of heating the reaction product above 105° C. is usually 0.5–5 hr. This preferred process of evaporating at least some of the ether is especially suitable when the ether is one which is completely miscible with water, e.g. dioxan or tetrahydrofuran.

Alternatively, but less preferred, the reaction mixture is heated at 40°–150° C., e.g. 90°–150° C., such as 105°–150° C. and especially 110°–150° C., usually for at least five minutes, such as five minutes to 24 hr, without evaporation of the ether, pressure being applied if necessary to keep the mixture liquid and stop the evaporation.

After the heating stage whether or not the ether has been evaporated, the reaction mixture is worked up to recover the tricycloalkyltin halide by contacting it with aqueous acid, e.g. water and a little acid, to hydrolyse any unreacted Grignard reagent and/or stannic halide to form an organic phase comprising the organotin product and the diluent and the ether (if present) and an aqueous acid phase comprising magnesium chloride and the ether, if present and if it is to any extent water soluble. The phases are separated. In the preferred process in which at least some of the ether has been evaporated, the reaction medium at the end of the reaction has a reduced ether content, which is advantageous as then most of the ether can be recovered during the evaporation and, if the ether is water soluble, only a reduced amount and ideally none is then lost into the aqueous phase. The tricycloalkyltin halide may be isolated from the organic phase. The aqueous phase may be stripped of volatile solvent, e.g. ether if present, and the ether reused.

Alternatively, the tricycloalkyltin halide with or without isolation from the organic phase may be converted directly into the corresponding hydroxide by hydrolysis, e.g. by contact with aqueous alkali such as sodium hydroxide and heating, e.g. to reflux. Thus the organic phase containing the tricycloalkyltin chloride may be added slowly over a period of 1–2 hr to an aqueous alkali solution at 70°–100° C., e.g. 80°–90° C., followed by reflux for 0.5–2 hr. At the end of the hydrolysis, any alkali metal halide not in aqueous solution may be dissolved by adding sufficient water. The hydrolysis product is then allowed to separate into an organic phase comprising the tricycloalkyltin hydroxide and an aqueous phase which are separated. The tricycloalkyltin hydroxide may then be recovered from the organic phase, e.g. by evaporation of solvent; it may be purified, e.g. by washing with water and/or recrystallization if desired.

A most preferred process of this invention comprises adding 2.8–3.05 molar proportions of cyclohexyl magnesium chloride in tetrahydrofuran to one molar proportion of stannic chloride in xylene, a weight percentage of stannic chloride to xylene of 10–25%, the addition being carried out with agitation at 70°–85° C. to give a reaction mixture from which a major proportion of the tetrahydrofuran is evaporated to give a medium comprising tricyclohexyltin chloride, the medium is treated with aqueous acid to give an aqueous phase and an organic phase comprising tricyclohexyltin chloride and the phases are separated.

The tricycloalkyltin halides or hydroxides produced by the process of the invention may be used as fungicides or an intermediates for making other tricyclo alkyltin compounds.

The invention is illustrated in the following Examples in which parts are parts by weight.

EXAMPLE 1

Cyclohexyl magnesium chloride was prepared in a reactor fitted with a stirrer, heater and reflux condenser, the contents of the reactor being maintained under a nitrogen atmosphere. The reactor was charged with 72.9 parts of magnesium and to this was added 10.0 parts cyclohexyl chloride, 8.1 parts cyclohexyl bromide, and 83.1 parts tetrahydrofuran. When the reaction had been initiated, a mixture of 339.6 parts of cyclohexylchloride and 670.7 parts tetrahydrofuran was added at a rate sufficient to maintain steady reflux. The mixture was then refluxed for 1 hr. The reaction mixture when cold was filtered leaving as filtrate a solution of cyclohexyl magnesium chloride in tetrahydrofuran.

A reactor fitted with a stirrer, heater, reflux condenser and with the contents maintained under nitrogen was charged with a solution of 260.7 parts stannic chloride in 1500 parts xylene. The solution was stirred and to it was added the solution of cyclohexyl magnesium chloride at a rate so that the reaction temperature did not exceed 85° C. initially and at a rate sufficient to maintain reflux when sufficient tetrahydrofuran has been added. At the end of the addition which took 1.5 hr, the reaction temperature was raised slowly to 120° C. with distillation of the tetrahydrofuran and the mixture refluxed at 120° C. for a total of 2 hrs since the end of the addition to give a mixture with a reduced content of tetrahydrofuran. The reaction mixture was cooled to 30° C. and to it was added a mixture of 645 parts water and 33.0 parts 30% hydrochloric acid with cooling. The organic phase produced was separated from the aqueous phase produced and filtered leaving a solution of tricyclohexyltin chloride, from which the chloride may be recovered by evaporation of the solvent.

The tricyclohexyltin chloride was converted into tricyclohexyltin hydroxide by addition of the organic solution of the chloride to a mixture of 45 parts sodium hydroxide, 45 parts water at 80°-85° C., over a period of 1½ hours. The mixture produced was refluxed for 1 hr and then cooled and 162 parts of water added to dissolve sodium chloride. The aqueous and organic phases produced were separated and the organic phase evaporated to dryness leaving a crude solid which was washed with water and dried to give 350 parts tricyclohexyltin hydroxide (90% pure and in 91% yield).

EXAMPLES 2-5 AND COMPARATIVE EXAMPLES A-C

The process for preparing tricyclohexyltin chloride as described in Example 1 was repeated with different amounts of tetrahydrofuran and xylene and/or different heat treatments at the end of the addition of the cyclohexyl magnesium chloride. In each case, a cyclohexyl Grignard reagent was prepared in tetrahydrofuran from magnesium (24.3g. 1g.atom) and added as in Example 1 to a solution of stannic chloride (86.9g., 0.33 mole) in xylene. At the end of the addition, the temperature was kept at 80° C. (for Example 4) or raised to the other temperatures specified in the Table below, with collection of THF distilled off in Ex. 3 and Ex. A only; the time for which the reaction was continued after the addition being the same, 2 hr in each case. At the end of the heat treatment in each case, the reaction mixture was worked up as in Ex. 1 and the organic phase analyzed by vapour phase chromotography (VPC). The solution of crude tricyclohexyltin chloride was evaporated and the crude yield of tricyclohexyltin chloride determined.

| Ex | Wt. of THF gms | Wt. of xylene gms | Weight % of SnCl$_4$ to xylene | Weight % of Grignard to THF | Weight % of xylene to xylene + THF | Temp. of heating after addition ° C | VPC analysis of product in Weight Percentages | | | Crude Yield gms. |
|---|---|---|---|---|---|---|---|---|---|---|
| | | | | | | | % cHex$_4$ Sn | % cHex$_3$ SnCl | % cHex$_2$ SnCl$_2$ | |
| 2 | 254.6 | 387.0 | 22.45 | 56.1 | 60.3 | 93 | 4.8 | 91.3 | 4.0 | 119.2 |
| 3 | 254.6 | 387.0 | 22.45 | 56.1 | 60.3 | 135 | 4.6 | 91.8 | 3.6 | 116.0 |
| A | 180.2 | 273.6 | 31.7 | 79.2 | 60.3 | 120 | 20.5 | 75.7 | 3.8 | 102.5 |
| B | 387.5 | 258.0 | 33.7 | 36.8 | 40.3 | 95 | 23.7 | 70.5 | 5.8 | 118.9 |
| 4 | 753.6 | 387.0 | 22.45 | 18.9 | 33.9 | 80 | 6.5 | 90.5 | 3.0 | 120.5 |
| 5 | 254.6 | 774.0 | 11.2 | 56.1 | 75.2 | 110 | 2.7 | 94.3 | 3.0 | 125.0 |
| C | 254.6 | 129.0 | 67.4 | 56.1 | 33.6 | about 90 | 28.0 | 66.8 | 5.1 | 117.0 | cHex in the above Table means cyclohexyl.
Ex. A - C are comparative.

The results in this Table show the great increase in yield and purity of the tricyclohexyltin chloride achieved with reactions involving solutions of SnCl$_4$ in xylene containing less than 25% SnCl$_4$ to xylene compared to those containing more than 25% SnCl$_4$:xylene.

We claim:

1. A process for preparing triorganotin halides, which comprises adding 3 ± 0.3 molar proportions of a cycloalkyl magnesium halide Grignard Reagent in which the cycloalkyl group is selected from the group consisting of cyclohexyl groups and alkyl cyclohexyl groups, in which there are 1-3 alkyl groups each of 1-4 carbon atoms, and in which the halide is selected from the group consisting of chloride, bromide and iodide, to one molar proportion of a stannic halide, in which the halide is selected from the group consisting of chloride, bromide and iodide, the cycloalkyl magnesium halide Grignard Reagent being dissolved in a completely water miscible ether solvent and the stannic halide being in an inert liquid diluent, said ether having a boiling point lower than that of said diluent, the weight percentage of stannic halide to said diluent being between 5% and 25%, the addition being carried out with agitation to form a reaction mixture comprising a tricycloalkyltin halide, evaporating at least some of said ether from said reaction mixture leaving a mixture depleted of ether, treating said reaction mixture depleted of ether with an aqueous acid to produce an organic phase comprising tricycloalkyltin halide and inert diluent, and an aqueous phase, and separating said phases.

2. A process according to claim 1 wherein the ether is tetrahydrofuran.

3. A process according to claim 1 wherein the diluent is a liquid hydrocarbon.

4. A process according to claim 3 wherein the diluent is xylene or toluene.

5. A process according to claim 3, wherein cyclohexyl magnesium chloride reacts with stannic chloride.

6. A process according to claim 1 wherein the addition of cycloalkyl magnesium halide to stannic halide is performed at 40°–105° C.

7. A process according to claim 1 wherein the weight percentage of diluent to the total of diluent and ether is 50–80%.

8. A process according to claim 1 wherein the reaction mixture is maintained at 90°–150° C. after the addition.

9. A process according to claim 8 wherein the reaction mixture is maintained at 105°–150° C. after the addition.

10. A process according to claim 1 wherein the weight percentage of stannic halide to diluent is 15–25%.

11. A process according to claim 1 wherein the weight percentage of stannic halide to diluent is 15–25%.

12. A process according to claim 1 which comprises adding 2.8–3.5 molar proportions of cyclohexyl magnesium chloride in tetrahydrofuran to one molar proportion of stannic chloride in xylene, a weight percentage of stannic chloride to xylene of 10–25%, the addition being carried out with agitation at 70°–85° C. to give a reaction mixture from which a major proportion of the tetrahydrofuran is evaporated to give a medium comprising tricyclohexyltin chloride, the mixture is treated with aqueous acid to give an aqueous phase and an organic phase comprising tricyclohexyltin chloride and the phases are separated.

13. A process according to claim 12 wherein the reaction mixture is heated to 90°–150° C. to evaporate the major proportion of tetrahydrofuran.

14. A process according to claim 1 wherein the triorganotin halide is treated with aqueous alkali to produce a triorganotin hydroxide.

15. A process according to claim 12 wherein an aqueous alkali is added to said organic phase comprising said tricyclohexyltin chloride to form tricyclohexyltin hydroxide.

16. A process according to claim 12 wherein up to 90% of said tetrahydrofuran is evaporated from said reaction mixture.

17. A process according to claim 1 wherein between 20% and 90% of said water miscible ether is evaporated from said reaction mixture.

* * * * *